(12) United States Patent
Prior

(10) Patent No.: US 11,166,749 B2
(45) Date of Patent: Nov. 9, 2021

(54) SURGICAL INSTRUMENTS WITH MULTI-PURPOSE DETACHABLE COMPONENTS

(71) Applicant: COVIDIEN LP, Mansfield, MA (US)

(72) Inventor: Scott J. Prior, Shelton, CT (US)

(73) Assignee: Covidien LP, Mansfield, MA (US)

(*) Notice: Subject to any disclaimer, the term of this patent is extended or adjusted under 35 U.S.C. 154(b) by 144 days.

(21) Appl. No.: 16/103,091

(22) Filed: Aug. 14, 2018

(65) Prior Publication Data

US 2019/0083133 A1 Mar. 21, 2019

Related U.S. Application Data

(60) Provisional application No. 62/559,118, filed on Sep. 15, 2017.

(51) Int. Cl.
*A61B 17/42* (2006.01)
*A61B 17/32* (2006.01)
(Continued)

(52) U.S. Cl.
CPC ...... *A61B 17/4241* (2013.01); *A61B 17/0218* (2013.01); *A61B 17/32002* (2013.01);
(Continued)

(58) Field of Classification Search
CPC ............ A61B 17/4241; A61B 18/1482; A61B 17/0218; A61B 18/00; A61B 17/32002; A61B 2018/142; A61B 2018/1412; A61B 2018/00601; A61B 2018/00208; A61B 2018/1475; A61B 2018/00559; A61B 2017/0225; A61B 2018/00202; A61B 2017/0417; A61B 2017/00477; A61B 2017/4233; A61B 2017/00557; A61B 17/42; A61B 17/12013; A61B 17/1285; A61B 17/320016; A61B 17/320036; A61B 2017/4225; A61B 2017/320024; A61B 2017/320028; A61B 2017/320032; A61B 2017/32004; A61B 2017/0046; A61B 2018/00255; A61B 2018/00607;
(Continued)

(56) References Cited

U.S. PATENT DOCUMENTS 3,926,192 A * 12/1975 Van Maren ........ A61B 17/4241
606/119
5,643,285 A * 7/1997 Rowden ............ A61B 17/4241
606/119
(Continued)

*Primary Examiner* — Kathleen S Holwerda
*Assistant Examiner* — Uyen N Vo
(74) *Attorney, Agent, or Firm* — Carter, DeLuca & Farrell LLP

(57) ABSTRACT

A uterine manipulator includes a shaft defining a proximal end portion and a distal end portion, a handle operably coupled to the proximal end portion of the shaft, and a distal assembly operably coupled to the distal end portion of the shaft. The distal assembly includes a colpotomy cup and an elongated tip extending distally from the colpotomy cup. At least a portion of the distal assembly is releasable from the distal end portion of the shaft and configured to engage tissue and to operably couple to a surgical tool to enable the surgical tool to perform at least one surgical task on tissue engaged by the at least a portion of the distal assembly.

15 Claims, 8 Drawing Sheets

(51) Int. Cl.
*A61B 18/00* (2006.01)
*A61B 17/02* (2006.01)
*A61B 18/14* (2006.01)
*A61B 17/00* (2006.01)
*A61B 17/04* (2006.01)

(52) U.S. Cl.
CPC .......... *A61B 18/00* (2013.01); *A61B 18/1482* (2013.01); *A61B 2017/00477* (2013.01); *A61B 2017/00557* (2013.01); *A61B 2017/0225* (2013.01); *A61B 2017/0417* (2013.01); *A61B 2017/4233* (2013.01); *A61B 2018/00202* (2013.01); *A61B 2018/00208* (2013.01); *A61B 2018/00559* (2013.01); *A61B 2018/00601* (2013.01); *A61B 2018/142* (2013.01); *A61B 2018/1412* (2013.01); *A61B 2018/1475* (2013.01)

(58) Field of Classification Search
CPC ............ A61B 2018/14; A61B 2018/15; A61B 2018/1452; A61B 19/5202; A61B 18/04; A61B 2017/00367; A61B 2017/4216–4225; A61B 18/00202; A61B 18/00559; A61B 18/00601; A61D 1/08; A61F 6/14–6/18
USPC ........................................................ 606/119
See application file for complete search history.

(56) References Cited

U.S. PATENT DOCUMENTS

| | | | |
|---|---|---|---|
| 5,746,750 A | 5/1998 | Prestel et al. | |
| 5,840,077 A | 11/1998 | Rowden et al. | |
| 8,025,670 B2 | 9/2011 | Sharp et al. | |
| 8,192,444 B2 | 6/2012 | Dycus | |
| 8,292,901 B2 | 10/2012 | Auerbach et al. | |
| 8,475,469 B2 | 7/2013 | Walter et al. | |
| 8,603,105 B2 | 12/2013 | Sauer | |
| 8,740,916 B2 | 6/2014 | Blair et al. | |
| 8,747,413 B2 | 6/2014 | Dycus | |
| 9,011,433 B2 | 4/2015 | Batchelor et al. | |
| 9,629,660 B2* | 4/2017 | Einarsson | A61B 17/32 |
| 2003/0187334 A1* | 10/2003 | Biswas | A61B 17/4241 600/227 |
| 2009/0131954 A1* | 5/2009 | Christian | A61B 17/4241 606/119 |
| 2010/0305578 A1* | 12/2010 | Auerbach | A61B 17/4241 606/119 |
| 2012/0109146 A1* | 5/2012 | Auerbach | 606/119 |
| 2013/0023896 A1* | 1/2013 | Quimby | A61B 17/4241 606/119 |
| 2014/0052144 A1 | 2/2014 | Singh et al. | |
| 2014/0257322 A1 | 9/2014 | Batchelor et al. | |
| 2014/0276812 A1* | 9/2014 | Batchelor | A61B 18/1485 606/48 |
| 2014/0358158 A1 | 12/2014 | Einarsson | |
| 2015/0005780 A1 | 1/2015 | Einarsson | |
| 2015/0127016 A1 | 5/2015 | Sauer | |
| 2015/0148812 A1 | 5/2015 | Ahluwalia | |
| 2016/0106463 A1* | 4/2016 | Egle | A61B 17/42 606/119 |
| 2016/0270819 A1* | 9/2016 | Ahluwalia | A61B 90/94 |
| 2018/0325552 A1* | 11/2018 | Weihe | A61B 17/32002 |

* cited by examiner

SURGICAL INSTRUMENTS WITH MULTI-PURPOSE DETACHABLE COMPONENTS

CROSS REFERENCE TO RELATED APPLICATION

The present application claims the benefit of and priority to U.S. Provisional Application Ser. No. 62/559,118, filed on Sep. 15, 2017 the entire contents of which are incorporated herein by reference.

TECHNICAL FIELD

The present disclosure relates to surgical instruments including multi-purpose detachable components. More specifically, the present disclosure relates to uterine manipulators including detachable components configured to detach from the uterine manipulators for use in the manipulation, breakdown, and/or removal of tissue.

BACKGROUND

Colpotomy is one of the final steps in laparoscopic hysterectomy and requires making a circular incision in vaginal tissue to separate the uterus from the vagina. Uterine manipulators are often utilized in laparoscopic hysterectomy procedures for, among other tasks, positioning the vagina such that the colpotomy can be performed and uterus removed. Uterine manipulators typically include a handle, a shaft extending distally from the handle, an occluder supported on the shaft for preventing the loss of insufflation gases, a colpotomy cup supported at a distal end of the shaft for positioning the cervix, and a tip portion that extends from the colpotomy cup and is configured for insertion through the cervix and into the uterus.

To perform the colpotomy, the shaft of the uterine manipulator is positioned within the vagina with the tip portion of the uterine manipulator extending into the uterus and the colpotomy cup disposed about the cervix to displace the cervix and enable formation of the colpotomy incision to separate the uterus from the vagina.

Once the colpotomy is complete and the uterus separated from the vagina, the uterus is manipulated, broken down, and/or removed. Access for instrumentation to manipulate, breakdown, and/or remove the uterus may be provided vaginally or through an abdominal port.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A uterine manipulator provided in accordance with the present disclosure includes a shaft defining a proximal end portion and a distal end portion, a handle operably coupled to the proximal end portion of the shaft, and a distal assembly operably coupled to the distal end portion of the shaft. The distal assembly includes a colpotomy cup and an elongated tip extending distally from the colpotomy cup. At least a portion, e.g., part of or the entirety of, the distal assembly is releasable from the distal end portion of the shaft, is configured to engage tissue, and is configured to operably couple to a surgical tool to enable the surgical tool to perform at least one surgical task on the engaged tissue.

In an aspect of the present disclosure, the entire distal assembly is releasable from the distal end portion of the shaft. In such aspects, the elongated tip may be configured to engage a surgical tissue cutting tool. Additionally or alternatively, the elongated tip and/or the colpotomy cup includes a tissue-engaging feature configured to inhibit rotation of tissue relative thereto.

In another aspect of the present disclosure, the distal assembly further includes a deployable anchor assembly. In such aspects, the deployable anchor assembly is the portion (or one of the portions) of the distal assembly that is releasable from the distal end portion of the shaft. The deployable anchor assembly may include a suture, a tissue-penetrating tip disposed at one end of the suture, and a tissue anchor disposed at a second end of the suture. Additionally or alternatively, the deployable anchor assembly may be configured to operably couple to a surgical grasper.

In yet another aspect of the present disclosure, an actuator is disposed on the handle and configured to release the at least a portion of the distal assembly.

Another uterine manipulator provided in accordance with the present disclosure includes a shaft defining a proximal end portion and a distal end portion, a handle operably coupled to the proximal end portion of the shaft, and a distal assembly operably coupled to the distal end portion of the shaft. The distal assembly includes a colpotomy cup and an elongated tip extending distally from the colpotomy cup and is releasable from the distal end portion of the shaft. The distal assembly is configured to engage tissue and to operably couple to a surgical tissue cutting tool to cut tissue engaged by the distal assembly.

In an aspect of the present disclosure, the elongated tip is configured to engage a surgical tissue cutting tool.

In another aspect of the present disclosure, the elongated tip defines threading configured to engage complementary threading of a surgical tissue cutting tool.

In still another aspect of the present disclosure, the elongated tip and/or the colpotomy cup include tissue-engaging features configured to inhibit rotation of tissue relative thereto.

In yet another aspect of the present disclosure, an actuator is disposed on the handle and configured to release the distal assembly.

Another uterine manipulator provided in accordance with the present disclosure includes a shaft defining a proximal end portion and a distal end portion, a handle operably coupled to the proximal end portion of the shaft, and a distal assembly operably coupled to the distal end portion of the shaft. The distal assembly includes a colpotomy cup, an elongated tip extending distally from the colpotomy cup, and a deployable anchor assembly. The deployable anchor assembly is releasable from the distal end portion of the shaft, is configured to engage tissue, and is configured to operably couple to a surgical grasper to enable the surgical grasper to manipulate tissue engaged by the deployable anchor assembly.

In an aspect of the present disclosure, the deployable anchor assembly includes a suture, a tissue-penetrating tip disposed at a first end of the suture, and a tissue anchor disposed at a second end of the suture. The suture may further include a grasping portion disposed towards the first end thereof. The grasping portion may be configured to facilitate grasping of the suture with a surgical grasper.

In another aspect of the present disclosure, the tissue anchor of the deployable anchor assembly includes a plurality of legs configured to inhibit passage of the tissue anchor through tissue.

In yet another aspect of the present disclosure, an actuation shaft extends through the elongated tip and is movable therethrough to deploy the deployable anchor assembly.

BRIEF DESCRIPTION OF THE DRAWINGS

Various aspects and features of surgical instruments including multi-purpose detachable components are described hereinbelow with reference to the drawings wherein like numerals designate identical or corresponding elements in each of the several views and.

DETAILED DESCRIPTION

The present disclosure provides surgical instruments, e.g., uterine manipulators, including multi-purpose detachable components. Although various configurations of uterine manipulators in accordance with the aspects and features of the present disclosure are detailed below, it is contemplated that the aspects and features of the present disclosure may likewise be utilized with any other suitable surgical instrument to provide additional functionality upon detachment of detachable components therefrom.

Figure 1A:
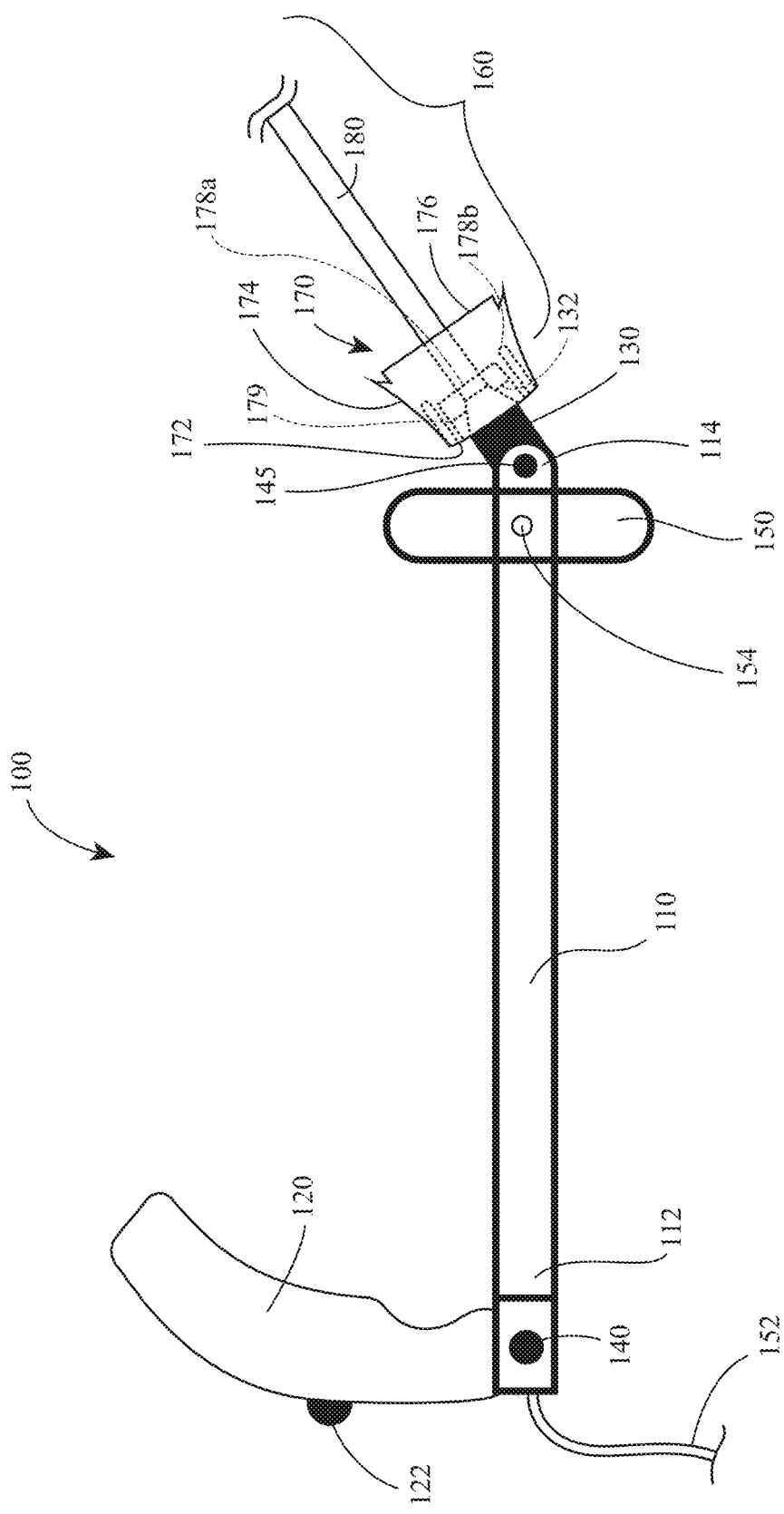
FIG. 1A is a side view of a uterine manipulator provided in accordance with the present disclosure with a distal assembly thereof engaged with the body thereof.
Figure 1B:
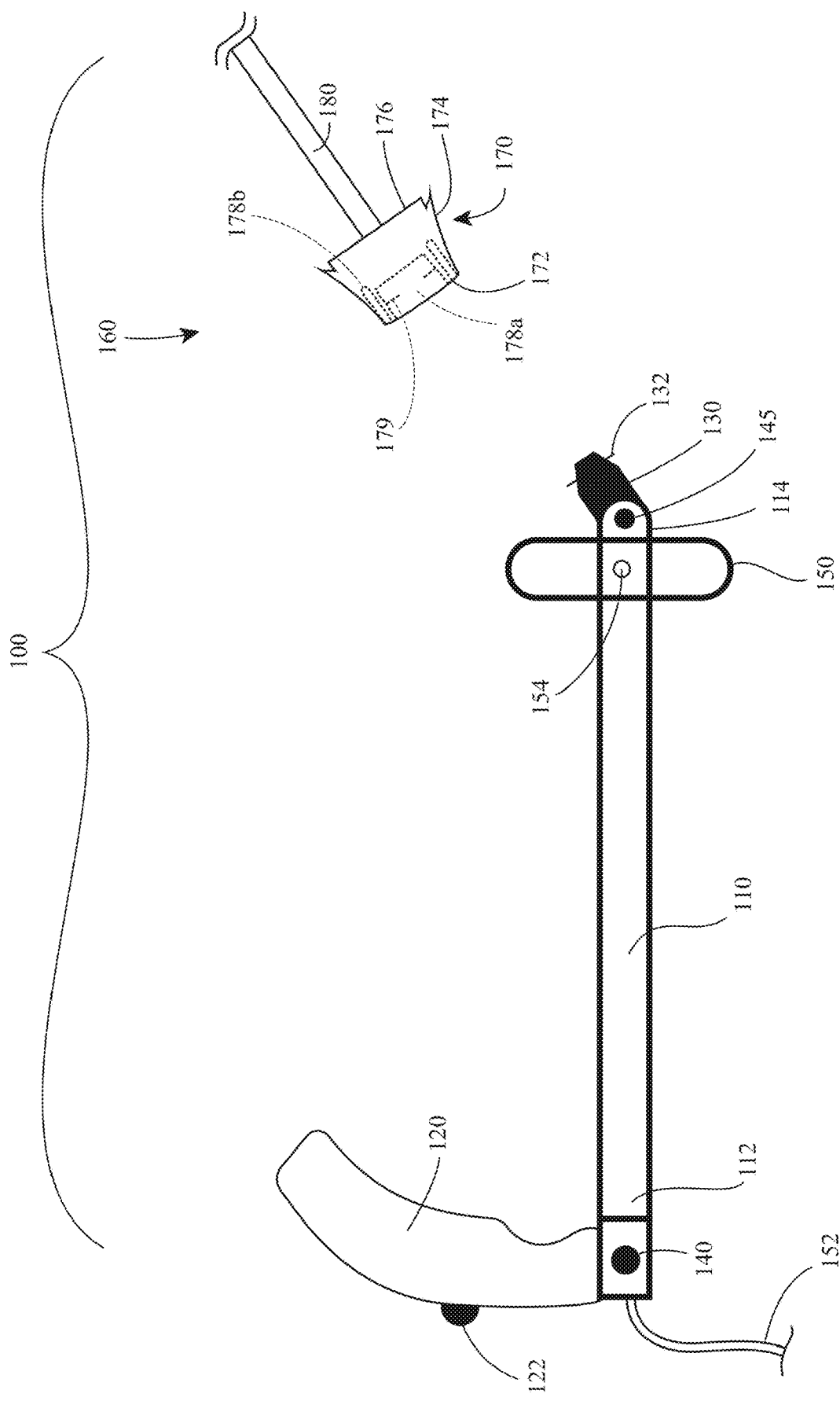
FIG. 1B is a side view of the uterine manipulator of FIG. 1A with the distal assembly disengaged from the body.

Turning to FIGS. 1A and 1B, a uterine manipulator provided in accordance with the present disclosure is shown generally identified by reference numeral 100. Uterine manipulator 100 includes a shaft 110, a handle 120 disposed at a proximal end portion 112 of shaft 110, and a distal connector 130 disposed at a distal end portion 114 of shaft 110. Uterine manipulator 100 further includes a proximal pivot 140 pivotably coupling handle 120 with shaft 110 at proximal end portion 112 of shaft 110 and a distal pivot 145 pivotably coupling distal connector 130 with shaft 110 at distal end portion 114 of shaft 110. Cables, linkages, or other suitable connectors (not shown) extend through shaft 110 and couple handle 120 with distal connector 130 to enable pivoting of distal connector 130 relative to shaft 110 in response to corresponding pivoting of handle 120 relative to shaft 110. Uterine manipulator 100 also includes an inflatable occlusion device 150 supported on shaft 120 towards a distal end portion thereof. Inflatable occlusion device 150 is adapted to connect to fluid source (not shown) by way of tube 152 and aperture 154 to enable selective inflation of inflatable occlusion device 150.

Continuing with reference to FIGS. 1A and 1B, uterine manipulator 100 additionally includes a distal assembly 160 that is releasably engageable with distal connector 130. Distal assembly 160 includes a colpotomy cup 170 and an elongated tip 180. Colpotomy cup 170 defines a proximal base 172 and a conical body 174 extending from proximal base 172, wherein conical body 170 defines a minimum diameter, to a free end 176, wherein conical body 174 defines a maximum diameter, although other configurations are also contemplated. Proximal base 172 of colpotomy cup 170 defines a recess 178a configured to at least partially receive distal connector 130 and may further include one or more tissue-engaging features 178b, e.g., spikes, configured to engage tissue and inhibit rotation thereof relative to colpotomy cup 170. Elongated tip 180 extends distally from proximal base 172, through conical body 174, and distally therefrom. Elongated tip 180 is described in greater detail below.

Distal connector 130 and colpotomy cup 170 include mutually-cooperating features 132, 179, e.g., pin(s) and corresponding aperture(s), snap-fit connectors, complementary threading, mating surfaces, etc. configured to enable releasable engagement of distal connector 130 within recess 178 of proximal base 172 of colpotomy cup 170 to releasably engage distal assembly 160 with the remainder of uterine manipulator 100. A release button 122 disposed on handle 120 may be provided to release the mutually-cooperating features 132, 179, thereby disengaging distal assembly 160 from distal connector 130. Cables, linkages, or other suitable connectors (not shown) extend through shaft 110 and couple release button 122 with distal connector 130 to enable disengagement of distal assembly 160 from distal connector 130 upon depression of release button 122. Alternatively, as opposed to active disengagement via depression of release button 122, mutually-cooperating features 132, 179 may be passively disengaged to enable removal of distal assembly 160 from distal connector 130, e.g., via moving distal assembly 160 and distal connector 130 in opposite directions. Uterine manipulator 100 may additionally or alternatively include other suitable features and/or components.

Figure 2A:
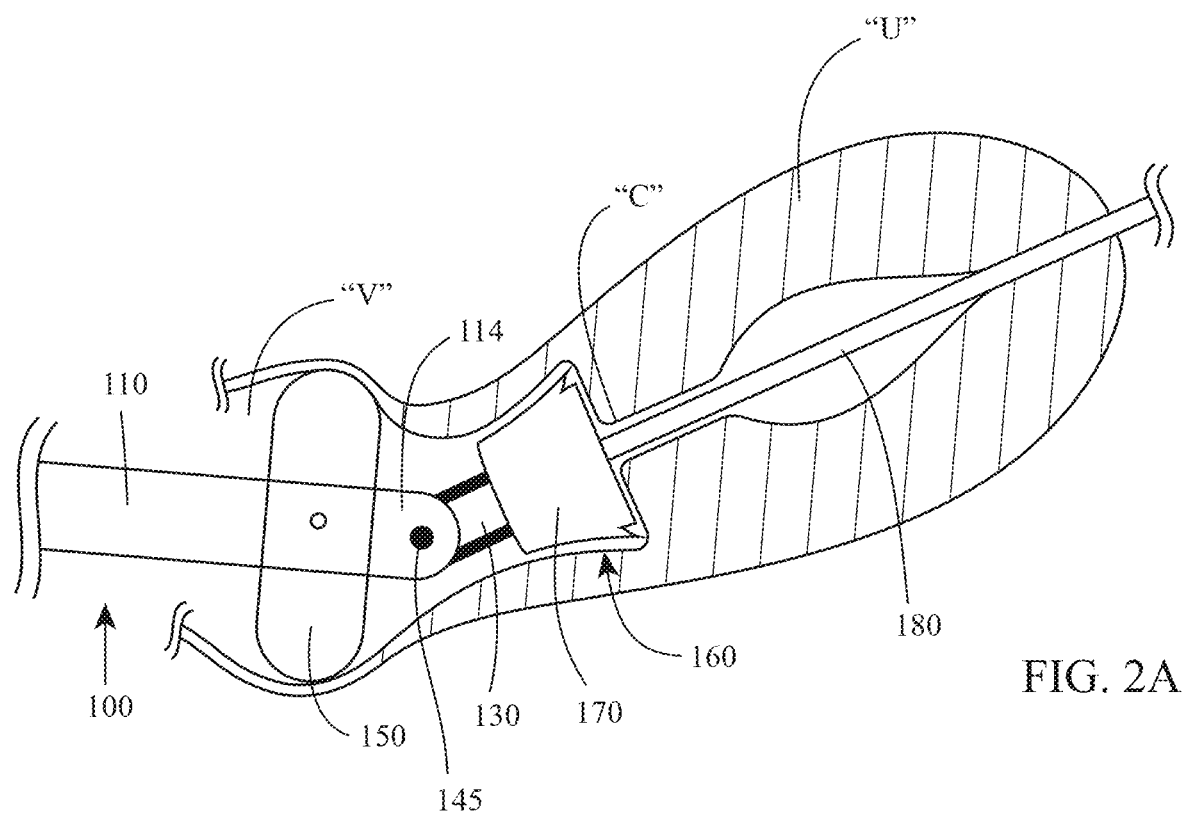
FIG. 2A is a longitudinal, cross-sectional view of a distal end portion of the uterine manipulator of FIG. 1A engaged with tissue to be removed perform separating the tissue.
Figure 2B:
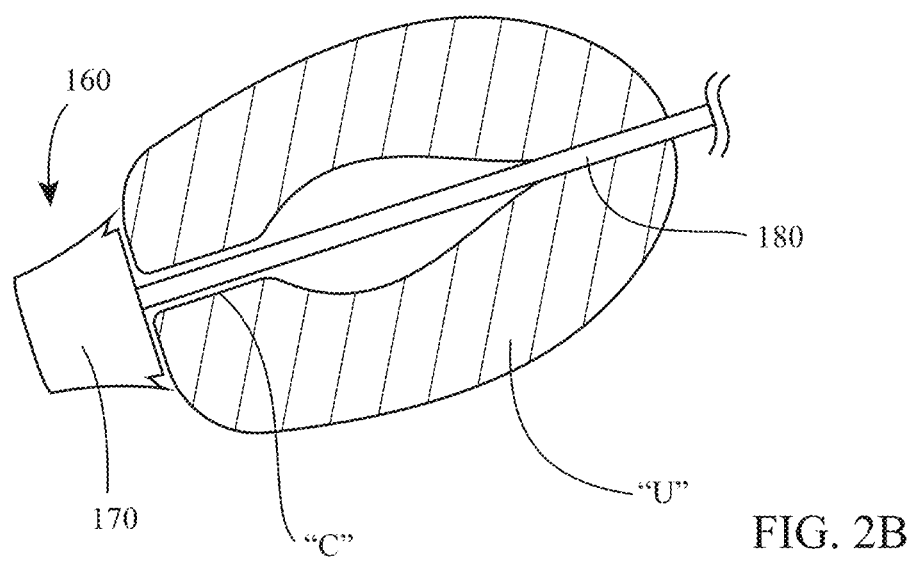
FIG. 2B is a longitudinal, cross-sectional view of the distal assembly of the uterine manipulator of FIG. 1A engaged with the tissue to be removed after separating the tissue.

With additional reference to FIGS. 2A and 2B, during use such as, for example, to perform a colpotomy, uterine manipulator 100 remains fully assembled; that is, distal assembly 160 remains engaged with distal connector 130 at the distal end of uterine manipulator 100. To perform the colpotomy, uterine manipulator 100 is positioned such that elongated tip 180 extends through the cervix "C" and into the uterus "U." Elongated tip 180 may perforate the uterus "U" and extend distally therefrom, in embodiments, to stabilize distal assembly 160 relative to the uterus "U." Colpotomy cup 170 is positioned about the cervix "C" and manipulated to displace the cervix "C." Occlusion device 150 may be inflated to maintain pneumoperitoneum and/or for stabilization, or may be deflated. Shaft 110 extends proximally through the vagina "V" and exteriorly thereof such that handle 120 remains exteriorized to enable manipulation by a user. Once the above-detailed position is achieved, as shown in FIG. 2A, the colpotomy may be performed to separate the uterus "U" from the vagina "V." Uterine manipulator 100 may be provided with features and/or additional instrumentation may be utilized to facilitate mechanical, electrical, or electromechanical colpotomy to separate the uterus "U" from the vagina "V."

Once the uterus "U" is separated from the vagina "V," and with distal assembly 160 engaged with tissue, e.g., with colpotomy cup 170 disposed about the cervix "C" and elongated tip 180 extending through the uterus "U," perforating the uterus "U," and extending distally therefrom, distal assembly 160 may be disengaged from the remainder of uterine manipulator 100, as shown in FIG. 2B, e.g., by depression of release button 122. With distal assembly 160 disengaged from uterine manipulator 100 (and still engaged with the uterus "U"), distal assembly 160 may be utilized to manipulate, breakdown, and/or facilitate removal of the uterus "U," as detailed below.

Figure 3:
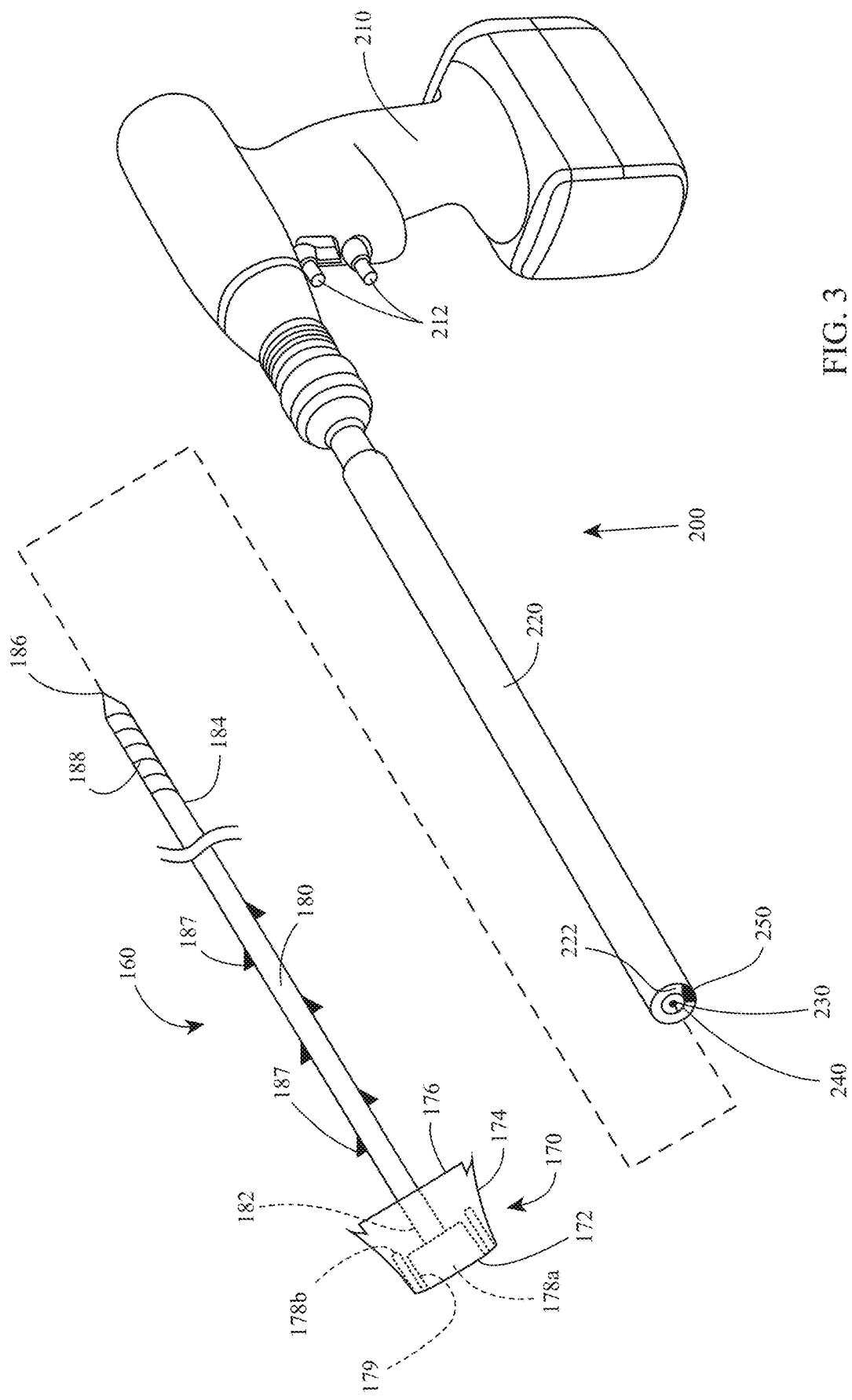
FIG. 3 is a front, perspective, exploded view illustrating the distal assembly of the uterine manipulator of FIG. 1A and a tissue cutting tool provided in accordance with the present disclosure and configured for use with the distal assembly.

Turning to FIG. 3, distal assembly 160, more specifically, may be configured to engage a tissue cutting tool 200 to facilitate breakdown and removal of the uterus "U" (FIGS. 2A-2B). Distal assembly 160, as detailed above, is releasable from uterine manipulator 100 and includes colpotomy cup 170 and elongated tip 180 although, in embodiments, colpotomy cup 170 may be maintained with uterine manipulator 100 and only elongated tip 180 disengaged therefrom.

Elongated tip 180 of distal assembly 160 includes a proximal end portion 182 that is engaged with colpotomy cup 170 at the proximal end thereof, and a distal end portion 184 that extends distally to a free distal end 186. Elongated tip 180 may include a plurality of tissue-engaging features 187, e.g., barbs, protrusions, etc., disposed along at least a portion of the length of proximal end portion 182 thereof. Tissue-engaging features 187 are configured to facilitate engagement of elongated tip 180 with tissue, e.g., the uterus, so as to inhibit rotation of the tissue relative to elongated tip 180 when elongated tip 180 extends through and in engagement with tissue. Elongated tip 180 may further include a tab, loop, or other suitable feature (not shown) to enable grasping of elongated tip 180 to manipulate distal assembly 160 and, thus, tissue engaged therewith.

Distal end portion 184 of elongated tip 180 may define threading 188 recessed into or protruding from an exterior surface thereof. Threading 188 is configured to engage complementary threading (not explicitly shown) protruding from or recessed into an interior surface of inner shaft 230 of tissue cutting tool 200 such that, upon relative rotation between elongated tip 180 and inner shaft 230, threading 188 engages the complementary threading of inner shaft 230 to secure elongated tip 180 relative to inner shaft 230. As an alternative to threaded-engagement, distal end portion 184 of elongated tip 180 may be configured to engage inner shaft 230 via any other suitable releasable engagement, e.g., snap-fit, bayonet coupling, pin-aperture engagement, etc.

Figure 4:
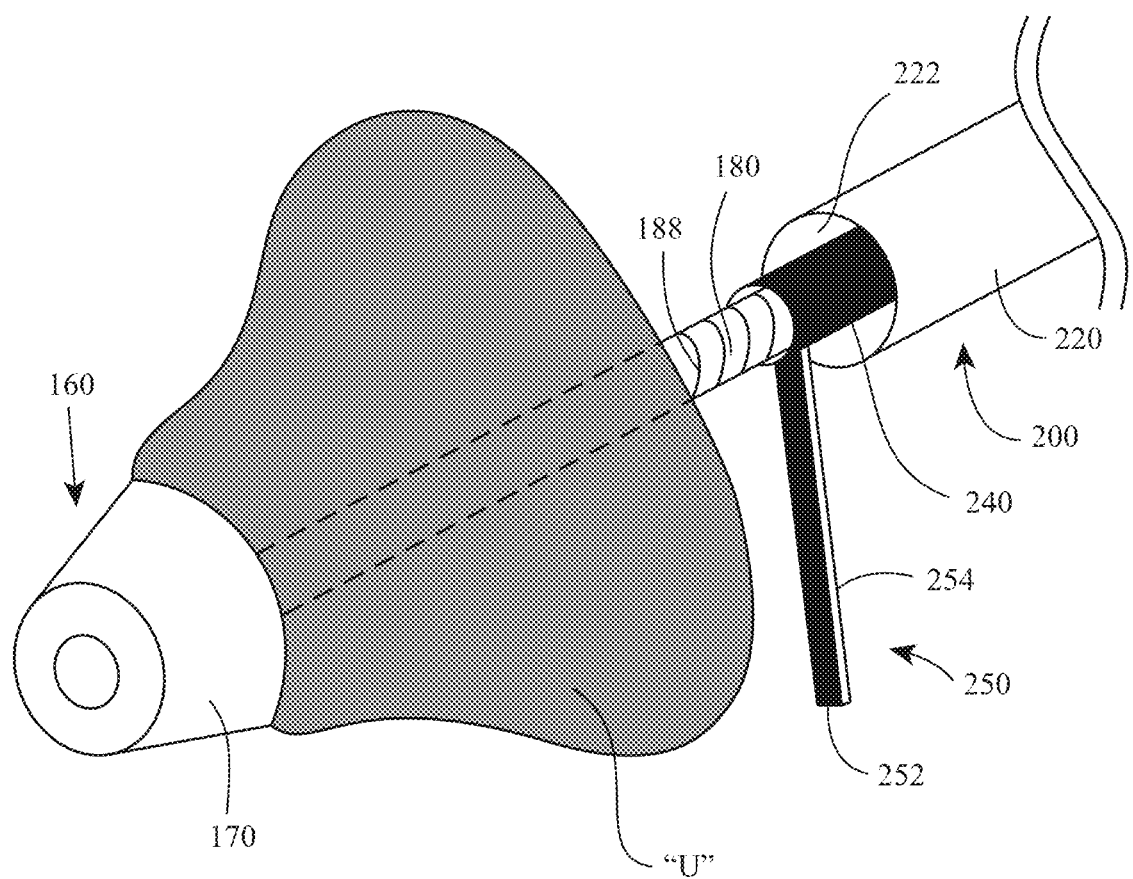
FIG. 4 is a front, perspective view of the distal assembly of the uterine manipulator of FIG. 1A engaged with the tissue cutting tool of FIG. 3 and including the tissue to be removed engaged thereon.

Continuing with reference to FIG. 3, tissue cutting tool 200 includes a handle assembly 210, an elongated tube 220 extending distally from handle assembly 210 and defining a longitudinal lumen 222, inner shaft 230 extending through longitudinal lumen 222 of elongated tube 220, and a sleeve 240 slidably and rotatably disposed about inner shaft 230. Sleeve 240 includes an end effector 250 (FIG. 4) disposed at a distal end portion thereof, as detailed below, although end effector 250 may alternatively be disposed at a distal end portion of elongated tube 220 and/or a distal end portion of inner shaft 230. Handle assembly 210 of tissue cutting tool 200 is operably coupled to sleeve 240 (or, alternatively, to inner shaft 230) to effect relative rotation between sleeve 240 and inner shaft 230. Handle assembly 210 may be powered, as illustrated, such that handle assembly 210 electromechanically rotates inner shaft 230, or may be manually driven. Handle assembly 210 further includes or is adapted to connect to a source of energy, e.g., a monopolar energy source (not shown), to facilitate electromechanical tissue cutting with end effector 250 (FIG. 4), although mechanical cutting is also contemplated. Actuators 212 disposed on handle assembly 210 are provided to enable the selective rotation of sleeve 240, deployment of sleeve 240 and end effector 250 (FIG. 4), and/or supply of energy to end effector 250 (FIG. 4). Handle assembly 210 additionally defines a proximal opening (not shown) in communication with longitudinal lumen 222 of elongated tube 220 to enable insertion of instrumentation, e.g., a tenaculum 400 (see FIG. 5), therethrough and/or to enable withdrawal of tissue proximally therefrom.

With additional reference to FIG. 4, end effector 250, as noted above, is disposed at a distal end portion of sleeve 240 and is selectively deployable, together with sleeve 240, from elongated tube 220, e.g., upon actuation of one or more of actuators 212. End effector 250 includes a leg 252 defining a cutting edge 254, which may be a mechanical, electromechanical, or electrical cutting edge. Leg 252 is operably engaged with a distal end portion of sleeve 240. End effector 250 is movable between a retracted position, wherein leg 252 is disposed within elongated tube 220 in generally longitudinally-extending orientation relative to a longitudinal axis of elongated tube 220 (and both inner shaft 230 and sleeve 240), and an extended position, wherein leg 252 extends distally from elongated tube 220 and is disposed in generally perpendicular orientation relative to the longitudinal axis of elongated tube 220 (and both inner shaft 230 and sleeve 240). Leg 252 may be formed from a shape memory material such that leg 252 assumes the extended position upon deployment from elongated tube 220, may include an articulation joint or resiliently flexible section, or may include any other suitable feature(s) to enable transition of leg 252 from the generally longitudinally-extending orientation to the generally perpendicular orientation upon deployment from elongated tube 220 and to return to the longitudinally-extending orientation upon retraction back into elongated tube 220.

With end effector 250 disposed in the extended position, one or more of actuators 212 may be actuated to rotate sleeve 240 relative to elongated tube 220 (by rotating either or both in opposite directions) such that leg 252 is rotated in a propeller-like motion, lead by cutting edge 254, to cut tissue within the cutting path of cutting edge 254 (a circular area defined within a plane) mechanically, electromechanically, or electrically. As noted above, colpotomy cup 170 and elongated tip 180 of distal assembly 160 include tissue-engaging features 178b, 187, respectively, to inhibit rotation of tissue relative to distal assembly 160, thus helping to ensure that cutting edge 254 is rotated relative to tissue and tissue is not rotated therewith. Further, colpotomy cup 170 serves as a distal base to inhibit tissue from sliding distally off of elongated tip 180. In embodiments where cutting edge 254 is energizable, cutting edge 254 may be formed at least partially from an electrically-conductive material and be energized upon rotation of end effector 250. Cutting edge 254 may be energized to serve as a monopolar electrode for use with a remote return pad (not shown) or may be one electrode in a bipolar configuration wherein the other electrode is an electrically-isolated portion of tissue cutting tool 200, distal assembly 160, or other instrument in the vicinity of cutting edge 254.

As illustrated in FIG. 4, with distal assembly 160 engaged with inner shaft 230 and engaging tissue, e.g., the uterus "U," thereon, sleeve 240 may be deployed and end effector 250 activated such that cutting edge 254 cuts an elongated strip from the uterus "U" about the outer perimeter thereof, similarly as an apple peeler operates. Elongated tube 220 may define an annular distal cutting edge to core tissue and facilitate passage thereof into lumen 222. The uterus "U" may be completely cut into elongated strips or only sufficiently so as to allow removal through elongated tube 220 or another suitable access opening (naturally occurring or surgically created). A tenaculum 400 (FIG. 5) may be inserted through elongated tube 220 to grasp tissue and draw the uterus "U" through the cutting path of cutting edge 254 and, ultimately, into elongated tube 220, to facilitate cutting and removal thereof.

Prior to or instead of elongated tip 180 of distal assembly 160 engaging tissue cutting tool 200 to enable breakdown and removal of the uterus "U," elongated tip 180 may instead be configured to engage another instrument, such as a manipulation device (not shown). The manipulation device may be utilized to manipulate and/or maneuver the distal assembly 160, including the uterus "U" thereon, to a desired position and/or for a desired purpose, e.g., to insert the uterus "U" into a containment bag (not shown), to retain the uterus "U" in position for morcellating by a separate tissue cutting tool, for inspection, etc. Further, it is contemplated that some or all of the above may be performed within a containment bag (not shown). Other suitable components and/or instrumentation for containment, breakdown, and/or removal may also be utilized.

Figure 5:
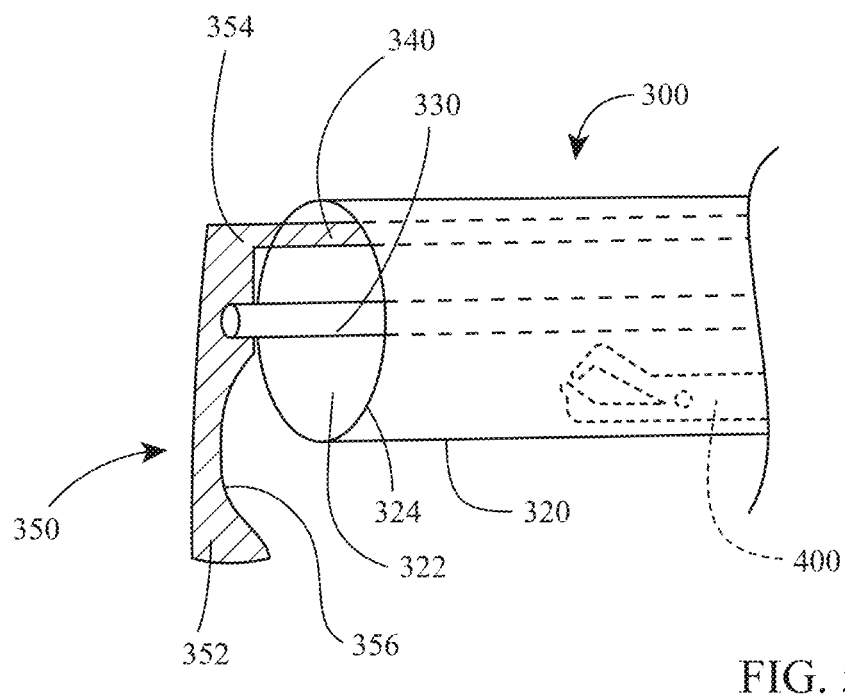
FIG. 5 is a side, perspective view of a distal end portion of another tissue cutting tool provided in accordance with the present disclosure and configured to engage the distal assembly of the uterine manipulator of FIG. 1A.

Turning now to FIG. 5, the distal end portion of another embodiment of a tissue cutting tool, which may include any of the aspects and features of tissue cutting tool 200 (FIG. 4), is shown as tissue cutting tool 300. As such, differences between tissue cutting tool 300 and tissue cutting tool 200 (FIG. 4) are described in detail hereinbelow.

Tissue cutting tool 300 includes a handle assembly (not shown, similar to handle assembly 210 of tissue cutting tool 200 (FIG. 4)), an elongated tube 320 extending distally from the handle assembly and defining a longitudinal lumen 322, and first and second shafts 330, 340 extending through longitudinal lumen 322 of elongated tube 320 in side-by-side relation relative to one another. More specifically, first shaft 330 may extend concentrically through elongated tube 320, while second shaft 340 extends offset relative to a longitudinal axis of elongated tube 320. Second shaft 340 includes an end effector 350 (FIG. 4) disposed at a distal end portion thereof.

Elongated tube 320 of tissue cutting tool 300 defines an annular tissue-cutting electrode 324 disposed about the perimeter thereof at the distal end portion thereof. Annular tissue-cutting electrode 324 is adapted to connect to a source of energy, e.g., a monopolar energy source (not shown), and is selectively energizable, e.g., upon activation of end effector 350, to cut tissue as it is drawn into elongated tube 320, to facilitate passage of tissue through longitudinal lumen 322. Alternatively, annular tissue-cutting electrode 324 may be a mechanical cutting surface, or may be omitted. Elongated tube 320 defines a sufficient diameter so as to enable tenaculum 400 to extend through longitudinal lumen 322 alongside first and second shafts 330, 340 for grasping and drawings tissue into and through longitudinal lumen 322.

First shaft 330 is configured to releasably engage elongated tip 180 of distal assembly 160, similarly as detailed above with respect to tissue cutting tool 200 (see FIG. 4), or in any other suitable manner. Alternatively, first shaft 330 (and, similarly, inner shaft 230 of tissue cutting tool 200 (FIGS. 1-4)) may be configured to receive any other suitable component (associated with a uterine manipulator, other surgical device, or an independent component) engaging tissue thereon to enable cutting and/or removal of tissue from an internal body cavity.

End effector 350 of tissue cutting tool 300 includes a cutting blade 352 pivotably coupled to a distal end portion of second shaft 340 via a hinge 354, although other configurations are also contemplated. As a result of this configuration, cutting blade 352 is selectively deployable from a retracted position, wherein cutting blade 352 is disposed within elongated tube 320 in generally longitudinally-extending orientation relative to the longitudinal axis of elongated tube 320 (and both first and second shafts 330, 340), and an extended position, wherein cutting blade 352 extends distally from elongated tube 320 and is disposed in generally perpendicular orientation relative to the longitudinal axis of elongated tube 320 (and both first and second shafts 330, 340). In the extended position, cutting blade 352 is offset relative to first shaft 330 so as not to interfere therewith. Cutting blade 352 defines a concave cutting edge 356 configured to mechanically cut tissue although, in embodiments, cutting blade 352 may additionally or alternatively be energizable (in monopolar fashion or bipolar fashion in conjunction with annular tissue-cutting electrode 324).

In use, with distal assembly 160 engaging the uterus "U" thereon (see FIG. 4) and engaged with first shaft 330, cutting blade 352 is extended to be positioned adjacent an outer surface of the uterus "U" (FIG. 4) and first shaft 330 is rotated relative to second shaft 340 (by rotating either or both in opposite directions) to thereby rotate the uterus "U" (FIG. 4) relative to cutting blade 352 such that cutting edge 356 skives along the outer surface of the uterus "U" (FIG. 4) and cuts an elongated strip of tissue therefrom. While first shaft 330 is rotated, tissue-cutting electrode 324 is energized to core tissue and facilitate passage thereof into lumen 322. Tenaculum 400 may be utilized to pull the uterus "U" into lumen 322 of elongated tube 320.

Referring generally to FIGS. 1A-5, in use, tissue cutting tools 200, 300 may be inserted through an abdominal port (not shown) and operably engaged with distal assembly 160 of uterine manipulator 100 (which, as can be appreciated, may be inserted vaginally), for cutting and removing tissue, e.g., the uterus "U" or portions thereof, through the abdominal port. As can appreciated, abdominal entry of tissue cutting tools 200, 300 is advantageous in that elongated tip 180 of distal assembly 160 is generally oriented towards the abdomen wall once positioned as detailed above, thus facilitating engagement thereof with tissue cutting tools 200, 300. However, other configurations are also contemplated.

Figure 6:
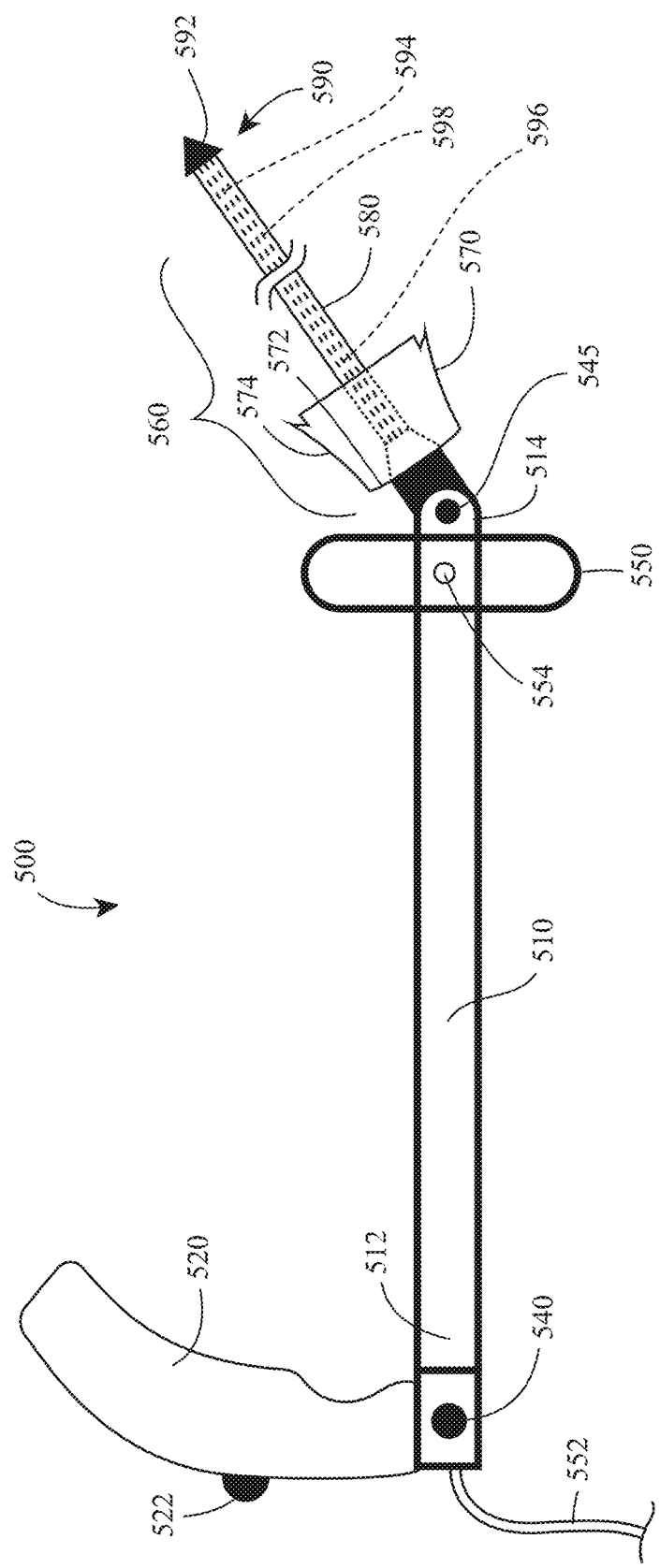
FIG. 6 is a side view of another uterine manipulator provided in accordance with the present disclosure with a distal assembly thereof engaged with the body thereof.

Turning to FIGS. 6-8C, and initially to FIG. 6, another uterine manipulator provided in accordance with the present disclosure is shown generally identified by reference numeral 500. Uterine manipulator 500 is similar to and may include any of the features of uterine manipulator 100 (FIGS. 1A and 1B), except as explicitly contradicted below.

Uterine manipulator 500 includes a shaft 510, a handle 520 disposed at a proximal end portion 512 of shaft 510, a distal assembly 560 extending distally from a distal end portion 514 of shaft 510, and a deployable anchor assembly 590 disposed at a distal end portion of distal assembly 560. Uterine manipulator 500 further includes a proximal pivot 540 pivotably coupling handle 520 with shaft 510 at proximal end portion 512 of shaft 510 and a distal pivot 545 pivotably coupling distal assembly 560 with shaft 510 at distal end portion 514 of shaft 510. Cables, linkages, or other suitable connectors (not shown) extend through shaft 510 and couple handle 520 with distal assembly 560 to enable pivoting of distal assembly 560 relative to shaft 510 in response to corresponding pivoting of handle 520 relative to shaft 510. Uterine manipulator 500 also includes an inflatable occlusion device 550 supported on shaft 520 towards a distal end portion thereof. Inflatable occlusion device 550 is adapted to connect to fluid source (not shown) by way of tube 552 and aperture 554 to enable selective inflation of inflatable occlusion device 550. Uterine manipulator 500 may also include a distal balloon (not shown) disposed on distal assembly 560, and/or other suitable features and/or components.

Continuing with reference to FIG. 6, distal assembly 560 includes a colpotomy cup 570, an elongated tip 580, and deployable anchor assembly 590. Colpotomy cup 570 defines a proximal base 572 and a conical body 574 extending from proximal base 572, similarly as detailed above with respect to colpotomy cup 170 (FIGS. 1A and 1B). Elongated tip 580 extends distally from proximal base 572, through conical body 574, and distally therefrom.

Figure 7:
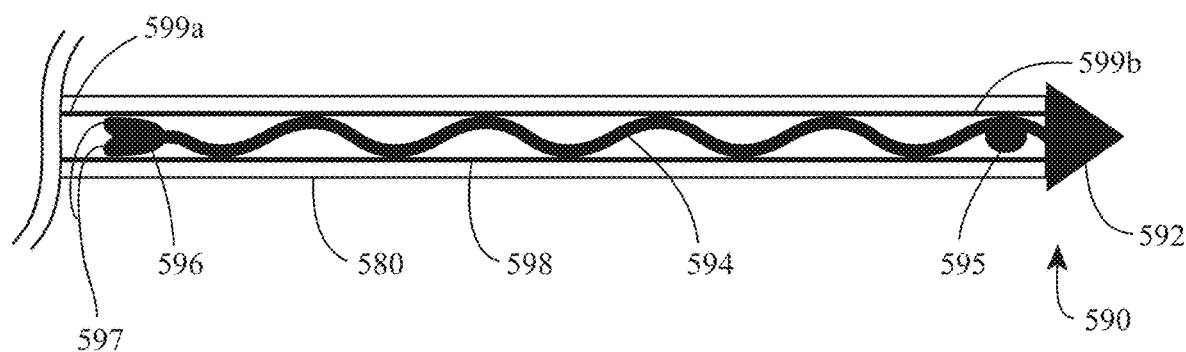
FIG. 7 is an enlarged, longitudinal, cross-sectional view of a distal assembly of the uterine manipulator of FIG. 6.

With additional reference to FIG. 7, deployable anchor assembly 590 includes a tissue-penetrating tip 592, a suture 594, and a tissue anchor 596, and includes an actuation shaft 598 associated therewith. Tissue-penetrating tip 592 may define any suitable configuration such as an arrow-head configuration or any other suitable configuration capable of penetrating tissue. In some embodiments, such as where tissue-penetrating tip 592 defines an arrow-head configuration, tissue-penetrating tip 592 is configured to penetrate tissue in a first direction and to inhibit backing out in a second, opposite direction once penetrated through tissue. Tissue-penetrating tip 592 is releasably coupled to elongated tip 580 of distal assembly 560 at a distal end portion thereof. Tissue-penetrating tip 592, more specifically, may be mounted on the distal end portion of elongated tip 580 or at least partially therein.

Suture 594 is engaged at a first end thereof to tissue-penetrating tip 592 and at a second end thereof to tissue anchor 596. Suture 594 may define a grasping portion 595, e.g., a looped portion, knotted portion, tab attached thereto, ring attached thereto, etc., to facilitate grasping of the first end of suture 594 with a grasping tool, e.g., surgical grasper 600 (FIG. 8C).

Tissue anchor 596, as noted above, is engaged to suture 594 at an opposite end of suture 594 relative to where tissue-penetrating tip 592 is engaged to suture 594. Tissue anchor 596 includes a plurality of fingers 597 and is configured to engage a surface of tissue to inhibit passage of tissue anchor 596 therethrough. More specifically, as suture 594 is pulled through tissue, tissue anchor 596 engaged a surface of the tissue such that, rather than tissue anchor 596 being pulled through tissue, tissue anchor 596 engages tissue to enable pulling of suture 594 to manipulate the tissue in a corresponding manner.

Actuation shaft 598 extends through elongated tip 580 of distal assembly 560 and, prior to deployment of deployable anchor assembly 590, retains suture 594 and tissue anchor 596 therein. Actuation shaft 598 defines a proximal end portion 599a and a distal end portion 599b. Proximal end portion 599a of actuation shaft 598 is coupled to a deployment button 522 disposed on handle 520 by way of cables, linkages, or other suitable connectors (not shown) extending through shaft 510. As such, actuation of deployment button 522 urges actuation shaft 598 distally such that distal end portion 599b of actuation shaft 598 is urged into contact with tissue-penetrating tip 592 to deploy tissue-penetrating tip 592 from the distal end of elongated tip 580. As an alternative to an active deployment such as that detailed above, tissue-penetrating tip 592 may be passively deployed, e.g., in response to proximal translation of uterine manipulator 500 relative to tissue when tissue-penetrating tip 592 is engaged with tissue. In such passive deployment embodiments, actuation shaft 598, deployment button 522, and the connectors extending therebetween need not be provided.

Figure 8A:
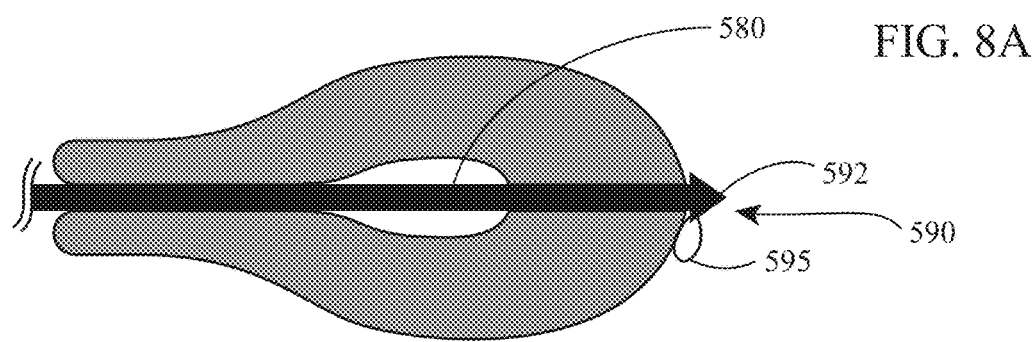
FIGS. 8A-8C are longitudinal, cross-sectional views of the distal assembly of FIG. 7 in use engaging tissue to be removed and manipulating the tissue for receipt within a containment bag, breakdown, and/or removal.
Figure 8B:
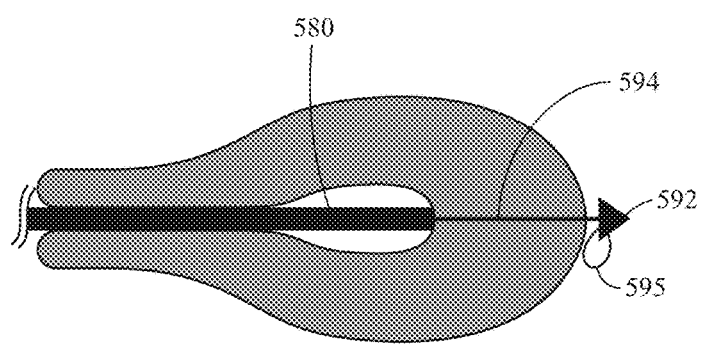
Figure 8C:
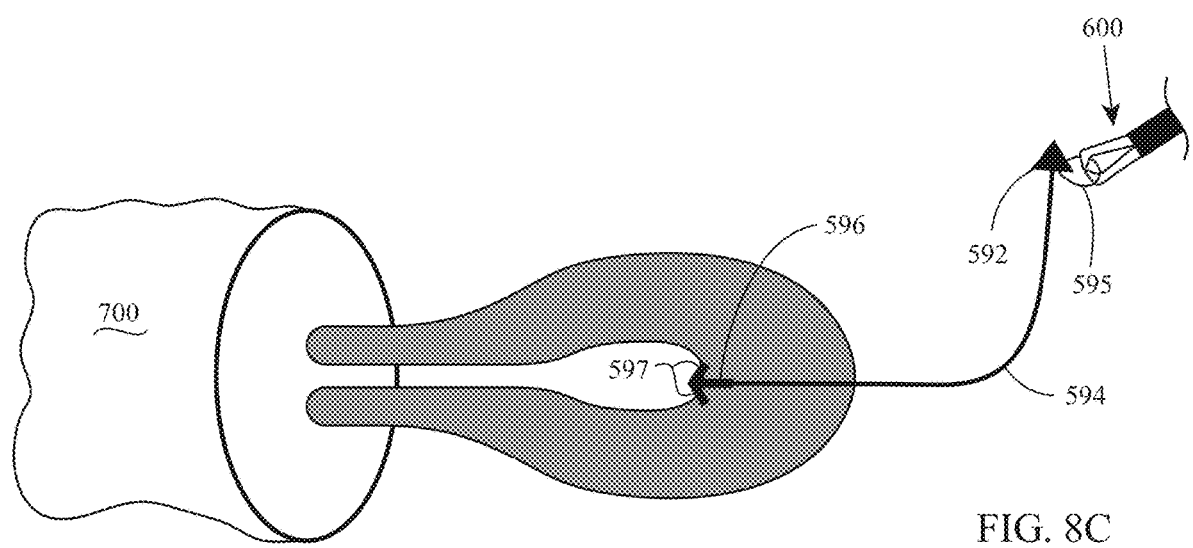

Turning to FIGS. 8A-8C, in conjunction with FIGS. 6 and 7, in use, uterine manipulator 500, similarly as detailed above, is positioned such that elongated tip 580 extends through the cervix "C" and into the uterus "U" in preparation for performing a colpotomy. In embodiments, elongated tip 580, lead by tissue-penetrating tip 592 of deployable anchor assembly 590, may perforate the uterus "U" and extend distally therefrom, to stabilize uterine manipulator 500. Colpotomy cup 570 is positioned about the cervix "C" and manipulated to displace the cervix "C." Occlusion device 550 may be inflated to maintain pneumoperitoneum and/or for stabilization, or may be deflated. Shaft 510 extends proximally through the vagina and exteriorly thereof such that handle 520 remains exteriorized to enable manipulation by a user. Once the above-detailed position is achieved, the colpotomy may be performed to separate the uterus "U" from the vagina, leaving elongated tip 580 and deployable anchor assembly 590 engaged with the detached uterus "U," as illustrated in FIG. 8A. Uterine manipulator 500 may be provided with features and/or additional instrumentation may be utilized to facilitate mechanical, electrical, or electromechanical colpotomy to separate the uterus "U" from the vagina.

Once the uterus "U" is separated from the vagina, and with tissue-penetrating tip 592 of deployable anchor assembly 590 engaged with the uterus "U," deployable anchor assembly 590 may be deployed via actuation of deployment button 522 (FIG. 6), in active deployment embodiments, or by proximal translation of uterine manipulator 500, in passive deployment embodiments. Once tissue-penetrating tip 592 is deployed from elongated tip 580 of uterine manipulator 500, uterine manipulator 500 may be withdrawn from the surgical site (vaginally) leaving tissue-penetrating tip 592 engaged with the uterus "U" on a distal side thereof, suture 594 extending through the uterus "U,", and tissue anchor 594 disposed on a proximal side of the uterus "U," as illustrated in FIG. 8B.

With uterine manipulator 500 withdrawn, tissue-penetrating tip 592 of deployable anchor assembly 590 is left engaged with the uterus "U" on a distal side thereof (from a vaginal entry perspective), suture 594 extends through the uterus "U," and tissue anchor 594 is disposed on a proximal side of the uterus "U" (from a vaginal entry perspective). Next or prior thereto, a surgical grasper 600 may be inserted through an abdominal port (not shown) and into the surgical site. Surgical grasper 600, more specifically, may be manipulated to grasp grasping portion 595 of suture 594 and pull grasping portion 595 proximally (from an abdominal entry perspective). Pulling grasping portion 595 in this manner pulls suture 594 proximally. During initial proximal pulling of suture 594, suture 594 is pulled proximally through the uterus "U" until tissue anchor 594 is moved into engagement with the uterus "U." Once tissue anchor 594 is moved into engagement with the uterus "U," fingers 597 engage the uterus "U" and inhibit passage of tissue anchor 594 therethrough. Thus, further manipulation of suture 594, e.g., via manipulation of surgical grasper 600, results in corresponding manipulation of the uterus "U." In this manner, the uterus "U" may be manipulated to facilitate positioning of the uterus "U" within a containment bag 700 (FIG. 8C), breakdown of the uterus "U," and/or removal of the uterus "U" from the internal surgical site (through an abdominal port or vaginally).

In embodiments, surgical grasper 600 may be inserted into a first opening of a containment bag, e.g., containment bag 700 (FIG. 8C), through the containment bag, and out a second opening of the containment bag such that the surgical grasper 600 may be utilized to grasp the tissue anchor 594 and pull the tissue anchor 594, together with the uterus "U," directly into the containment bag. As can be appreciated, such a configuration facilitates loading of the uterus into the containment bag.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A uterine manipulator, comprising:
   a shaft defining a proximal end portion and a distal end portion;
   a distal connector pivotally coupled to the distal end portion of the shaft;
   a handle operably coupled to the proximal end portion of the shaft; and
   a distal assembly operably coupled to the distal connector, the distal assembly including a colpotomy cup and an elongated tip extending distally from the colpotomy cup, the elongated tip defining a longitudinal axis, the elongated tip including a plurality of barbs spaced apart from each other along the longitudinal axis of the elongated tip, the plurality of barbs configured to inhibit rotation of the elongated tip relative to tissue engaged by the plurality of barbs, the colpotomy cup defining a recess configured to removably receive the distal connector therein,
   wherein the colpotomy cup of the distal assembly is releasable from the distal connector by removing the distal connector from the recess of the colpotomy cup, and wherein at least a portion of the distal assembly is configured to engage tissue and to operably couple to a surgical tool to enable the surgical tool to perform at least one surgical task on tissue engaged by the at least a portion of the distal assembly.

2. The uterine manipulator according to claim 1, wherein the entire distal assembly is releasable from the distal end portion of the shaft.

3. The uterine manipulator according to claim 2, wherein the elongated tip is configured to engage a surgical tissue cutting tool.

4. The uterine manipulator according to claim 2, wherein the colpotomy cup includes at least one protrusion configured to inhibit rotation of the colpotomy cup relative to tissue engaged by the at least one protrusion.

5. The uterine manipulator according to claim 1, further comprising an actuator disposed on the handle, the actuator configured to release the at least a portion of the distal assembly.

6. A uterine manipulator, comprising:
   a shaft defining a proximal end portion and a distal end portion;
   a distal connector pivotally coupled to the distal end portion of the shaft;
   a handle operably coupled to the proximal end portion of the shaft; and
   a distal assembly operably coupled to the distal connector, the distal assembly including a colpotomy cup and an elongated tip extending distally from the colpotomy cup, the elongated tip defining a longitudinal axis, the elongated tip including a plurality of barbs spaced apart from each other along the longitudinal axis of the elongated tip, the plurality of barbs configured to inhibit rotation of the elongated tip relative to tissue engaged by the plurality of barbs, the colpotomy cup defining a recess configured to removably receive the distal connector therein,
   wherein the colpotomy cup of the distal assembly is releasable from the distal connector by removing the distal connector from the recess of the colpotomy cup, and wherein the distal assembly is configured to engage tissue and to operably couple to a surgical tissue cutting tool to cut tissue engaged by the distal assembly.

7. The uterine manipulator according to claim 6, wherein the elongated tip is configured to engage a surgical tissue cutting tool.

8. The uterine manipulator according to claim 7, wherein the elongated tip defines threading configured to engage complementary threading of a surgical tissue cutting tool.

9. The uterine manipulator according to claim 6, wherein the colpotomy cup includes at least one protrusion configured to inhibit rotation of the colpotomy cup relative to tissue engaged by the at least one protrusion.

10. The uterine manipulator according to claim 6, further comprising an actuator disposed on the handle, the actuator configured to release the distal assembly.

11. A distal assembly configured for use with a uterine manipulator, comprising:
    a colpotomy cup including a proximal base and a conical body extending from the proximal base;
    an elongated tip extending from the colpotomy cup, the elongated tip defining a longitudinal axis, the elongated tip including a plurality of barbs spaced apart from each other along the longitudinal axis of the elongated tip, the plurality of barbs configured to inhibit rotation of the elongated tip relative to tissue engaged by the plurality of barbs; and
    a recess formed in the colpotomy cup, the recess configured to releasably connect with a complimentary distal connector pivotally coupled to a distal end portion of a uterine manipulator, wherein the colpotomy cup is releasable from the distal connector by removing the distal connector from the recess,
    wherein at least a portion of the distal assembly is configured to engage tissue and to operably couple to a surgical tool to enable the surgical tool to perform at least one surgical task on tissue engaged by the at least a portion of the distal assembly.

12. The distal assembly of claim 11, wherein the elongated tip is configured to engage a surgical tissue cutting tool.

13. The distal assembly of claim 11, wherein the colpotomy cup includes at least one protrusion configured to inhibit rotation of the colpotomy cup relative to tissue engaged by the at least one protrusion.

14. The distal assembly of claim 11, wherein the elongated tip extends distally from a distal end of the colpotomy cup.

15. The distal assembly of claim 11, wherein the elongated tip defines threading configured to engage complementary threading of a surgical tissue cutting tool.

* * * * *